(12) United States Patent
Wutz et al.

(10) Patent No.: US 7,842,415 B2
(45) Date of Patent: Nov. 30, 2010

(54) TERMINAL CONNECTOR FOR CONNECTING A CELL TO A MEDICAL DEVICE

(75) Inventors: David Wutz, Williamsville, NY (US); Gary Freitag, East Aurora, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 12/813,563

(22) Filed: Jun. 11, 2010

(65) Prior Publication Data
US 2010/0248017 A1 Sep. 30, 2010

Related U.S. Application Data

(62) Division of application No. 11/164,508, filed on Nov. 28, 2005, now Pat. No. 7,749,651.

(51) Int. Cl.
*H01M 2/06* (2006.01)
*H01M 2/30* (2006.01)

(52) U.S. Cl. ........................ 429/180; 429/181

(58) Field of Classification Search ................. 429/180, 429/181
See application file for complete search history.

(56) References Cited
U.S. PATENT DOCUMENTS

| | | | |
|---|---|---|---|
| 3,833,421 A | 9/1974 | Rubischko et al. | |
| 4,042,759 A | 8/1977 | Cella | |
| 4,203,201 A | 5/1980 | Mead et al. | |
| 4,217,403 A | 8/1980 | O'Boyle et al. | |
| 4,242,425 A | 12/1980 | O'Boyle et al. | |
| 4,508,797 A | 4/1985 | Knoedler et al. | |
| 4,609,598 A | 9/1986 | Tucholski et al. | |
| 5,500,026 A | 3/1996 | Heller et al. | |
| 5,789,101 A * | 8/1998 | Wheeler et al. | ................ 429/98 |
| 5,792,573 A * | 8/1998 | Pitzen et al. | ................... 429/97 |
| 2003/0091893 A1 | 5/2003 | Kishiyama et al. | |

FOREIGN PATENT DOCUMENTS

JP  2005274319  10/2005

* cited by examiner

*Primary Examiner*—Gregg Cantelmo
(74) *Attorney, Agent, or Firm*—Michael F. Scalise (57) ABSTRACT

A electrical connector for connection to an electrochemical cell is described. The connector comprises a conductive lid; a ferrule disposed within an opening through the conductive lid; a conductive center pin disposed within the ferrule; and a hermetic seal formed between the pin and an interior surface of the ferrule. A mating terminal connector adapted to be connected to the ferrule and the conductive center pin is further provided. The terminal connector is a device for easily and quickly connecting the cell to a circuit board of the kind found in an implantable medical device, such as a cardiac pacemaker, defibrillator, neuro-stimulator, drug pump, and the like.

8 Claims, 8 Drawing Sheets

TERMINAL CONNECTOR FOR CONNECTING A CELL TO A MEDICAL DEVICE

CROSS-REFERENCE TO RELATED APPLICATION

This application is a divisional of U.S. patent application Ser. No. 11/164,508, filed on Nov. 28, 2005, now U.S. Pat. No. 7,749,651, to Wutz et al.

BACKGROUND OF THE INVENTION

1. Field of the Invention

The present invention relates generally to a terminal connector or connector assembly for connection to an electrochemical cell. More particularly, the present invention relates in one embodiment to a terminal connector for attaining a simple, reliable connection of a device to a high capacity, high energy density cell used in implantable medical devices. The terminal connector connects to the cell's terminal assembly disposed on the exterior of the cell. That way, the terminal assembly occupies very little of the internal volume of the cell.

2. Description of Related Art

A case-grounded implantable electrochemical cell most commonly provides two terminals of opposed polarity for connection of the cell to a device to be powered. One terminal extends from a glass-to-metal seal, and the other terminal extends from the case. Prior art terminals are disadvantageous in that one of the terminals typically protrudes inwardly into the cell casing, thereby reducing the casing volume available for containing the active cell materials. The use of prior art terminals thus results in a reduction of the overall cell volumetric efficiency. Additionally, the connection of the cell terminals to the device to be powered is typically accomplished by soldering, welding, or wire-bonding the cell terminals to the device.

For both the central terminal pin extending from the glass-to-metal seal, and the case grounding terminal that is welded or otherwise joined to the cell casing, each is comprised of a fine wire extending outwardly from the casing. These wires are fragile and are thus susceptible to displacement and fracture by bending during cell handling. Additionally, it is difficult to position the terminal wires precisely and to maintain such positioning in the event they are to be matched with specific corresponding terminals of the device to be powered by the cell when making connection with such a device. The terminal wires are easily bent and misaligned during handling of the cell prior to connection to the device.

Heretofore, a number of patents and publications have disclosed cells including terminal connections to powered devices. For example, U.S. Pat. No. 5,250,373 to Muffoletto et al., which is assigned to the assignee of the present invention and incorporated herein by reference, describes an electrochemical cell including a central lead that is fixed relative to a lid by a generally cylindrical ferrule element, which is fitted at one end to an opening in the lid and secured to the lid by welding. The space between the lead and the ferrule is filled by a glass seal that extends along the major portion of the length of the ferrule. This glass-to-metal seal insulates the lead electrically from the lid and the cell casing, and seals the lead so that no egress or ingress of gases or liquids into or out of the casing can occur. The entire glass-to-metal seal is disposed beneath the lid on the interior of the cell casing. This assembly thus occupies space within the cell casing that could be more advantageously used for active materials, which would increase the cell's volumetric efficiency and capacity.

Additionally, U.S. Pat. No. 6,004,692 to Muffoletto et al., which is assigned to the assignee of the present invention and incorporated herein by reference, describes an electrochemical cell including an electrode assembly constructed of a serpentine electrode with interleaved counter electrode plates. The electrochemical cell disclosed therein also includes a glass-to-metal seal assembly similar to that disclosed in the aforementioned U.S. Pat. No. 5,250,373 to Muffoletto et al., wherein the lead is connected to the interleaved cathode plates by a cathode bridge. These are only two examples of many conventionally constructed electrochemical cells having the glass-to-metal seal assembly disposed beneath the lid on the interior of the casing, thus using space within the cell that could be more advantageously used for active materials.

SUMMARY OF THE INVENTION

There is therefore a need for an electrical terminal connector for attaining a simple, reliable connection to the terminal assembly of a high capacity, high energy density cell used in implantable medical devices, wherein the terminal assembly is exterior of the cell, and occupies very little, if any, of the valuable internal volume of the cell that is better used to contain active materials.

Accordingly, embodiments of the present invention are provided that meet at least one or more of the following objects of the present invention.

It is an object of this invention to provide a cell for use in an implantable medical device that includes a terminal assembly that is external to the cell casing.

It is a further object of this invention to provide a cell that includes a terminal assembly that is simple to connect to and disconnect from a terminal connector connectable to an implantable medical device.

It is a further object of this invention to provide a cell for connection to a device that includes a terminal connector that is simple to connect to a circuit board of the device.

It is a further object of this invention to provide a cell for use in an implantable medical device that includes a terminal connector that is connectable to a corresponding mating fitting of the device, wherein the mating fitting is a standardized, mass-produced fitting.

According to the present invention, therefore, a terminal connector is provided for connection to a cell. The cell includes a conductive lid comprised of a wall having an inside surface, an outside surface, and an opening therethrough from the inside surface to the outside surface. The cell comprises a ferrule of a conductive hollow cylindrical body having a central axis, an interior surface, an exterior surface, an outer end, and an inner end. The inner end is electrically joined and sealed within the opening through the wall of the conductive lid and is substantially coplanar with the inside surface of the wall of the conductive lid; the cell further includes a conductive center pin or terminal pin comprising an elongated surface, an inner end, and an outer end. The terminal pin is disposed within the hollow cylindrical body of the ferrule and aligned along the central axis thereof, thereby forming an annular cavity between the elongated surface of the terminal pin and the interior surface of the ferrule. A hermetic glass-to-metal seal is formed in the annular cavity.

The inner end of the ferrule is preferably joined to the lid by a seam weld that is flush with the inside surface of the lid. The exterior surface of the ferrule may be threaded to enable connection with a correspondingly threaded terminal connector of the present invention. Alternatively, the exterior surface of the ferrule may be provided with small protruding pins to enable connection with a BNC terminal connector of the present invention. The conductive lid, the ferrule, and the center pin may be made of titanium, or of stainless steel. In the latter instance, the terminal pin may be made of molybdenum.

Also according to the present invention, a terminal connector is provided for connection to the ferrule electrically joined to the casing and for connection to the insulated conductive terminal pin. The terminal connector comprises a non-conductive cap including a hollow cylindrical body covered at an outer end by a flange, a center terminal embedded in the flange, and a perimeter terminal disposed within the hollow cylindrical body of the cap. When the terminal connector is connected to the ferrule, the exterior surface of the ferrule is in contact with the perimeter terminal of the terminal connector, and the cell's terminal pin is in contact with the center terminal of the terminal connector. This provides opposite polarity electrical conduction through the terminal pin and through the body of the ferrule.

If the exterior surface of the ferrule is threaded, the perimeter terminal of the terminal connector is correspondingly threaded to enable a threaded connection between the terminal connector and the ferrule. If the exterior surface of the ferrule is provided with small protruding pins, the terminal connector is formed as a BNC connector adapted to engage with the protruding pins of the ferrule. If the exterior surface of the ferrule is provided with a smooth cylindrical surface, the perimeter terminal of the terminal connector is provided with a smooth inner surface dimensioned such that the terminal connector is press-fittingly engageable with the exterior surface of the ferrule. If a permanent, rather than detachable electrical connection between the ferrule and the terminal connector is desired, the perimeter terminal of the terminal connector may be joined to the exterior surface of the ferrule by a weld. In this embodiment, a cap of the terminal connector is preferably made of a ceramic material rather than a plastic, in order to prevent damage to the cap during the welding process.

To facilitate connection of the terminal connector to an external device to be powered by the cell, the terminal connector preferably further comprises a first conductor extending from the center terminal through a flange of the cap, and a second conductor extending from the perimeter terminal through the cap flange. In one preferred embodiment, the first and second conductors are comprised of elongated tabs adapted for connection into an electrical receptacle. The electrical receptacle typically is comprised of a pair of slots in a circuit board dimensioned to permit the elongated tabs of the conductors to be "plugged" into them. The center contact, the perimeter contact, and the electrical conductor of the terminal connector may be made of stainless steel or titanium.

Also according to the present invention, an electrochemical cell is provided comprising a conductive casing closed at one end and having an opening at the opposite end thereof closed by a conductive lid, the conductive lid is comprised of a wall having an inside surface, an outside surface, and an opening therethrough from the inside surface to the outside surface; an electrode assembly housed inside the casing and comprised of a first electrode of a first polarity and including a current collector; a second electrode of a second, opposite polarity; an electrolyte provided in the casing to activate the electrode assembly; a ferrule comprised of a conductive hollow cylindrical body having a central axis, an interior surface, an exterior surface, an outer end, and an inner end, the inner end electrically joined and sealed within the opening through the wall of the conductive lid and being substantially coplanar with the inside surface of the wall of the conductive lid; a conductive center terminal pin comprising an elongated surface, an inner end electrically connected to the current collector, and an outer end, the terminal pin disposed within the hollow cylindrical body of the ferrule and aligned along the central axis thereof, thereby forming an annular cavity between the elongated surface of the terminal pin and the interior surface of the ferrule; and a hermetic seal formed in the annular cavity. The electrochemical cell may further include the aforementioned terminal connector.

The electrochemical cell may be configured with a case-negative or case-positive ground configuration, the former being preferred. The case-negative cell may be comprised of a simple rectilinear electrode structure, or the electrodes may be configured in a serpentine or jellyroll arrangement. In the serpentine arrangement, the cell may further comprise a cathode bridge to facilitate connection of a current collector to the multiple cathode plates interleaved between the folds of the serpentine anode.

The terminal connectors of the present invention are advantageous because they provide a simple, reliable connection to high capacity, high energy density electrochemical cells, such as e.g., those used in implantable medical devices. The terminal connectors of the present invention are connectable to terminal assemblies disposed on the exterior of the cell. Electrochemical cells using the terminal connectors of the present invention can therefore contain a greater amount of active materials, thereby increasing the incapacity and energy density.

The foregoing and additional objects, advantages, and characterizing features of the present invention will become increasingly more apparent upon a reading of the following detailed description together with the included drawings.

BRIEF DESCRIPTION OF THE DRAWINGS

The present invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by the appended claims.

DETAILED DESCRIPTION OF THE PREFERRED EMBODIMENTS

For a general understanding of the present invention, reference is made to the drawings. In the drawings, like reference numerals have been used throughout to designate identical elements. In describing the present invention, a variety of terms are used in the description.

As used herein, the term "active material" is meant to indicate a cathode or anode material used in an electrochemical cell, which participates in the oxidation-reduction reaction(s) therein, thereby resulting in the discharge of energy from the electrochemical cell.

The present invention provides a direct and simple means of connecting a cell to a device. The present invention adapts the terminal feed-through system that is used in case-grounded implantable grade cells. That system includes a glass-to-metal seal comprising a cylindrical metal ferrule, a non-conductive hermetic sealing material, and a centralized terminal pin. The pin and ferrule are of opposed polarity and are electrically insulated from one another with the hermetic sealing material. The seal also holds the terminal pin concentric with the ferrule and hermetically separates the internal cell components from their outside environment. Typically, the ferrule is contained within the cell body, and cannot be used as a terminal circuit connector.

In that respect, the cell's terminal assembly is characterized by a cylindrical metal ferrule that protrudes from the outer surface of the casing, and the cell lid in particular. The ferrule is made of the same conductive material as the casing and lid to which it is joined. The terminal assembly is configured to accept a mating terminal connector connected to the circuitry of the device to be powered by the cell. The ferrule of the cell's terminal assembly thus eliminates the need to provide a second terminal pin extending from the cell lid or casing.

The outer and inner geometry of the ferrule may be threaded or straight walled, but must correspond with the configuration of the mating terminal connector connectable to the device to be powered. The ferrule may be configured for a mechanical connection (e.g., a press-fit, a threaded, of a BNC-type connection), or a soldered, brazed, or welded connection.

Figure 1:
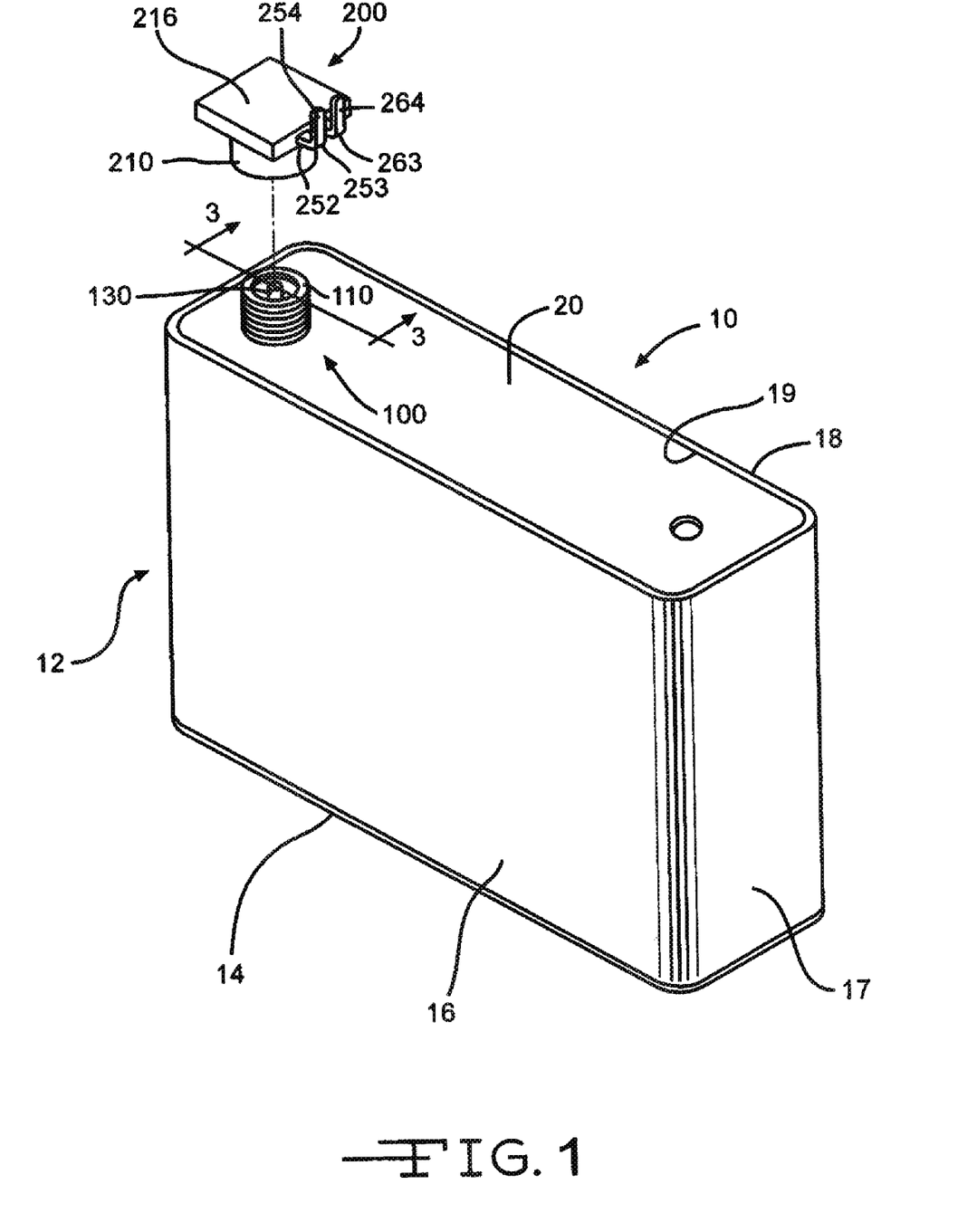
FIG. 1 is a perspective view of one electrochemical cell including a cell terminal assembly and a mating terminal connector of the present invention separated from the cell's terminals.
Figure 2:
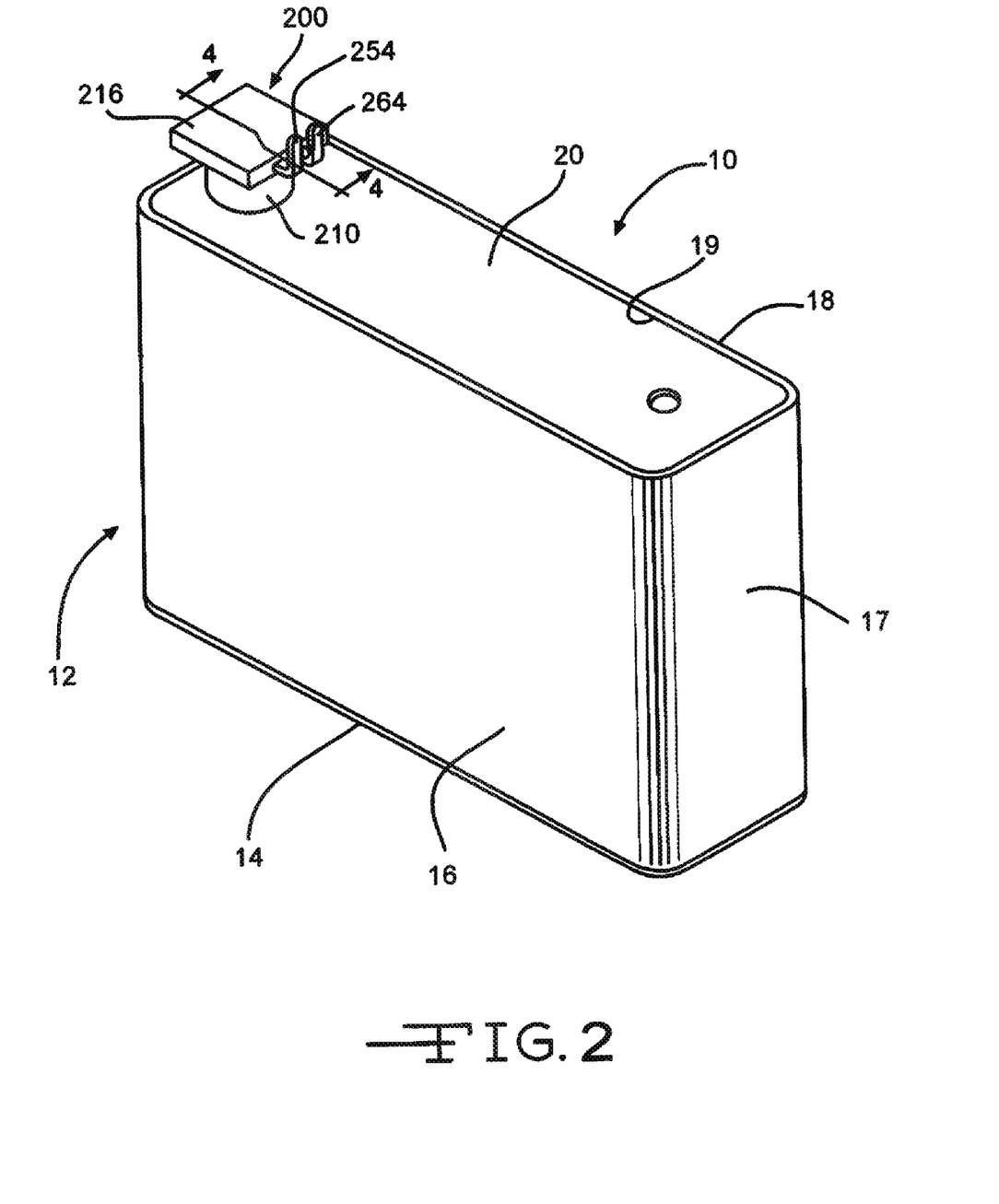
FIG. 2 is a perspective view of the cell mated to the terminal connector of FIG. 1.

FIG. 1 is a perspective view of one electrochemical cell including a cell terminal assembly and a mating terminal connector. FIG. 2 is a perspective view of the cell and mating terminal connector of FIG. 1, wherein the mating terminal connector is shown connected to the cell. Cell 10 is comprised of a conductive casing 12 closed at lower end 14, and having walls 16 and 17, and an opening 19 at the upper end 18 thereof. The casing 12 is closed at opening 19 by a conductive lid 20, which is sealed to casing 12 by suitable means such as e.g. seam weld 15 (see FIG. 3). Cell 10 further comprises an electrode assembly housed inside casing 12 and comprised of a first electrode of a first polarity including a current collector 40, a second electrode of a second, opposite polarity (not shown), and an electrolyte (not shown) provided in the casing 12 to activate the electrode assembly.

Figure 3:
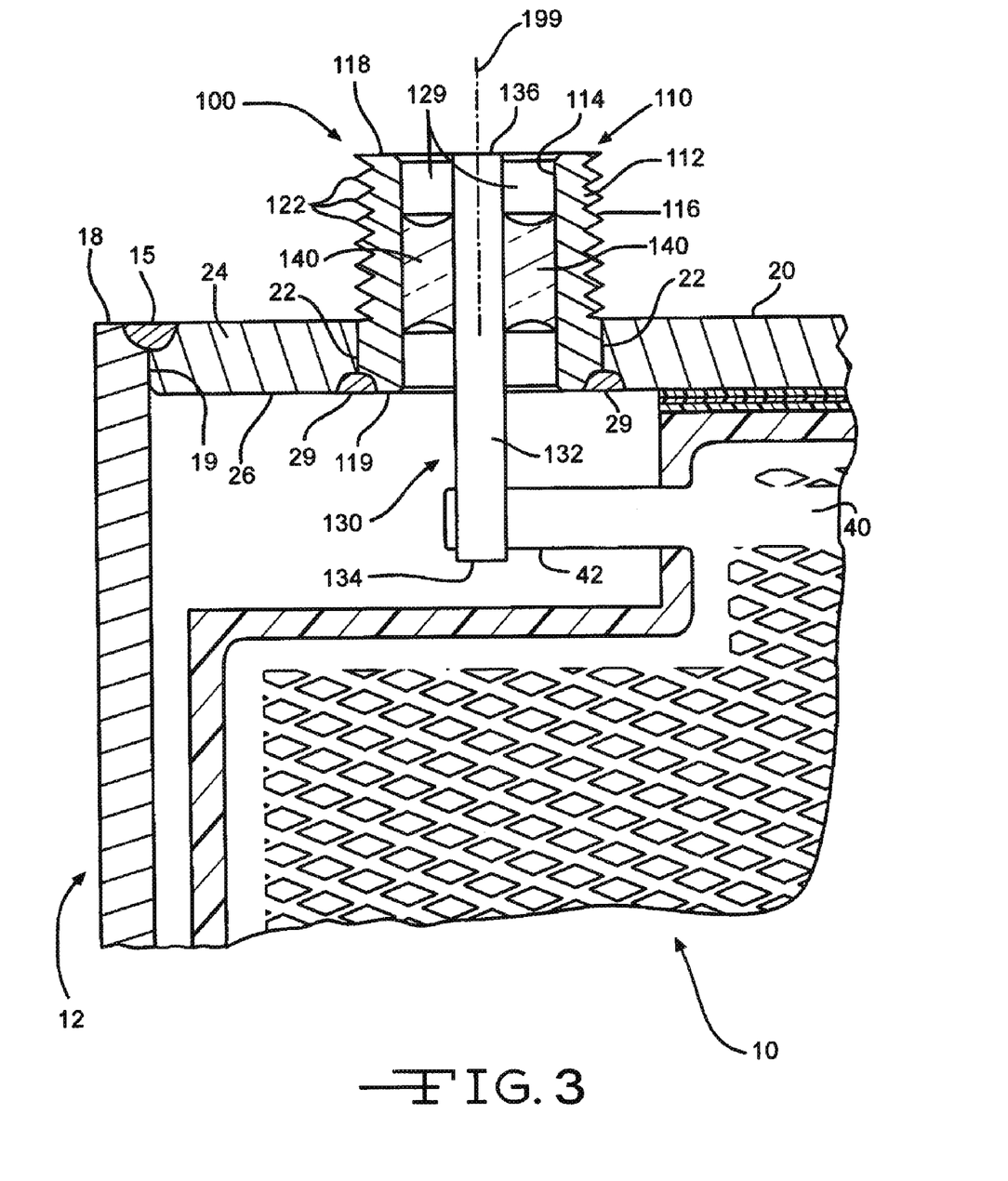
FIG. 3 is a side cross-sectional view of the cell's terminal assembly taken along line 3-3 of FIG. 1.

FIG. 3 is a side cross-sectional view of the cell terminal assembly taken along line 3-3 of FIG. 1. The terminal assembly 100 comprises a ferrule 110 comprised of a conductive hollow cylindrical body 112 having a central axis 199, an interior surface 114, an exterior surface 116, an outer end 118, and an inner end 119, the inner end 119 electrically joined and sealed within an opening 22 through the wall 24 of the conductive lid 20 and substantially coplanar with the inside surface 26 of the lid wall 24. The coaxial connector assembly 100 further comprises a conductive terminal pin 130 comprising an elongated surface 132, an inner end 134, and an outer end 136. The pin 130 is disposed within the hollow cylindrical body 112 of the ferrule 110 and aligned along the central axis 199 thereof, thereby forming an annular cavity 129 between the elongated surface 132 of the terminal pin 130 and the interior surface 114 of the ferrule 110. Ferrule 110 and center pin 130 are thus coaxial, sharing a common central axis 199.

Coaxial connector assembly 100 further comprises a hermetic sealing material 140 disposed in the annular cavity 129 to form a glass-to-metal seal (GMTS) with the ferrule 110 and terminal pin 130. As used herein, a GMTS is to be considered as being completely impervious to the passage of liquid or gas either into or out of the cell, and completely resistant to corrosion or other degradation by materials within the cell, or in the external environment. The sealing material 140 is formed of electrically insulative material, so that terminal pin 130 is electrically insulated from ferrule 110. In one preferred embodiment, the sealing material 140 is a glass seal, such as is described and shown in the aforementioned U.S. Pat. No. 5,250,373 to Muffoletto et al.

The inner end 119 of ferrule 110 is preferably joined to lid 20 by a peripheral seam weld 29 that is flush with the inside surface 26 of the lid 20. Ferrule 110 is thus electrically connected and sealed to lid 20.

Terminal pin 130 is electrically connected to one of the electrodes of cell 10. In the embodiment depicted in FIG. 3, terminal pin 130 extends downwardly into the cell 10, and terminal pin 130 is joined to a coupling element 42 extending from the current collector 40 by suitable means such as e.g., welding. In other embodiments, the coupling element 42 of current collector 40 may be formed as a hollow sleeve, and the inner end 134 of terminal pin 130 may be roughened and fitted within a sleeve, as is shown and described in the aforementioned U.S. Pat. No. 6,929,881 to Wutz et al.

It is preferable that the conductive materials of connector assembly 100 are made of the same material as the lid 20. In one embodiment in which lid 20 is made of titanium, ferrule 110 and center pin 130 are also made of titanium. In another embodiment in which lid 20 is made of stainless steel, ferrule 110 is made of stainless steel. In this embodiment terminal pin 130 may also made of stainless steel, or molybdenum. It is to be understood that these materials are to be considered exemplary, and not limiting, and that other suitable metallic materials may be used that are formable to precise dimensions and resistant to degradation by materials within the cell and/or materials in the external environment.

Figure 4:
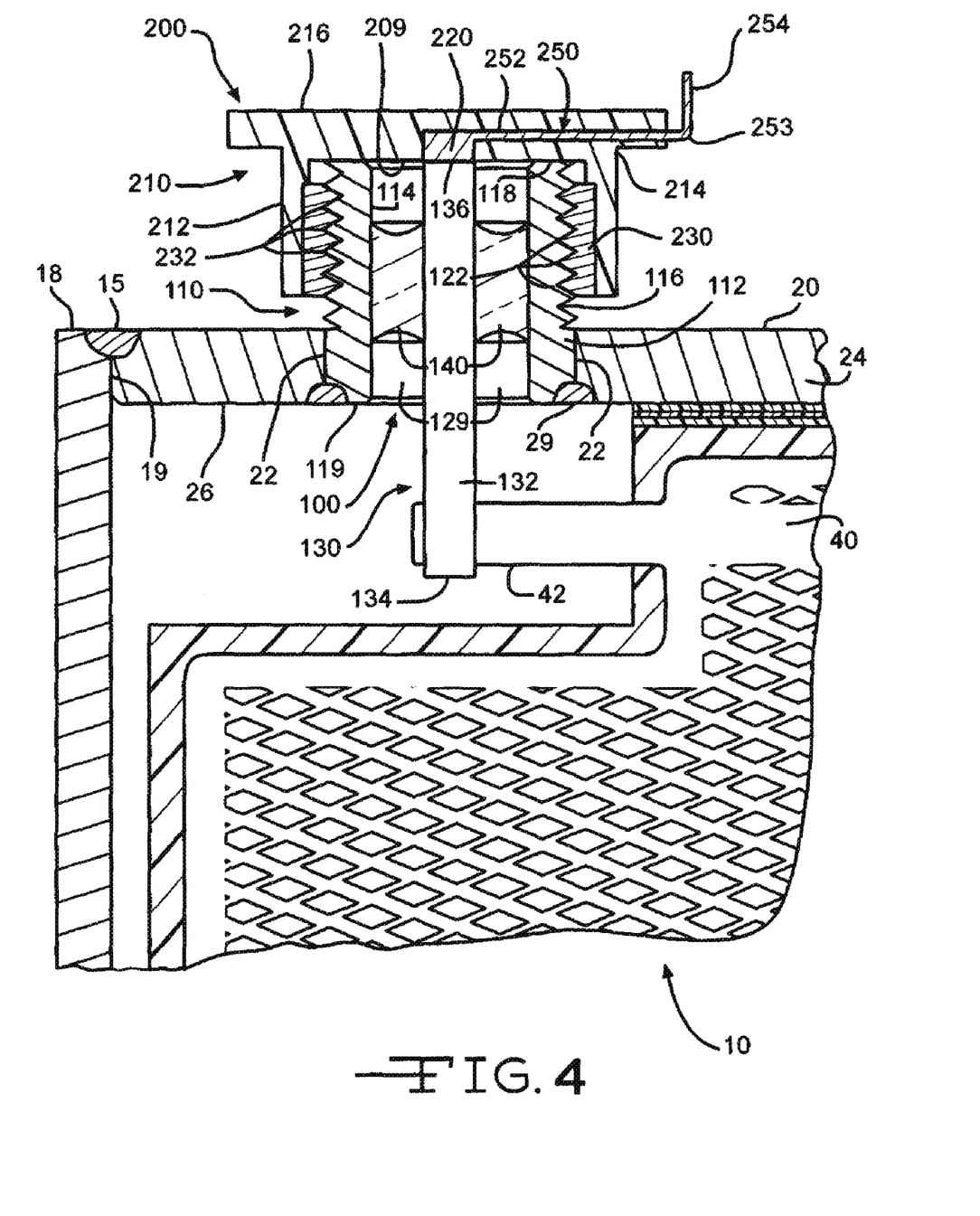
FIG. 4 is a side cross-sectional view taken along line 4-4 of FIG. 2 showing the cell's terminal assembly mated to the terminal connector.

FIG. 4 is a side cross-sectional view of the cell's terminal assembly 100 connected to the mating terminal connector 200. The mating terminal connector 200 is adapted to be connected to coaxial connector assembly 100, and more specifically, the ferrule 110 and the conductive center pin 130 thereof. Terminal connector 200 is comprised of a non-conductive cap 210 including a hollow cylindrical body 212 covered at an outer end 214 by a flange 216, a center terminal 220 embedded in the flange 216, and a perimeter terminal 230 disposed within the hollow cylindrical body 212 of the cap 210. When the mating terminal connector 200 is connected to the ferrule 110, the exterior surface 116 of the ferrule 110 is brought into contact with the perimeter terminal 230 and the terminal pin 130 is brought into contact with the center terminal 220, thereby enabling electrical conduction from the cell 10 through the center terminal pin 130 and through the body 112 of the ferrule 110.

Figure 4A:
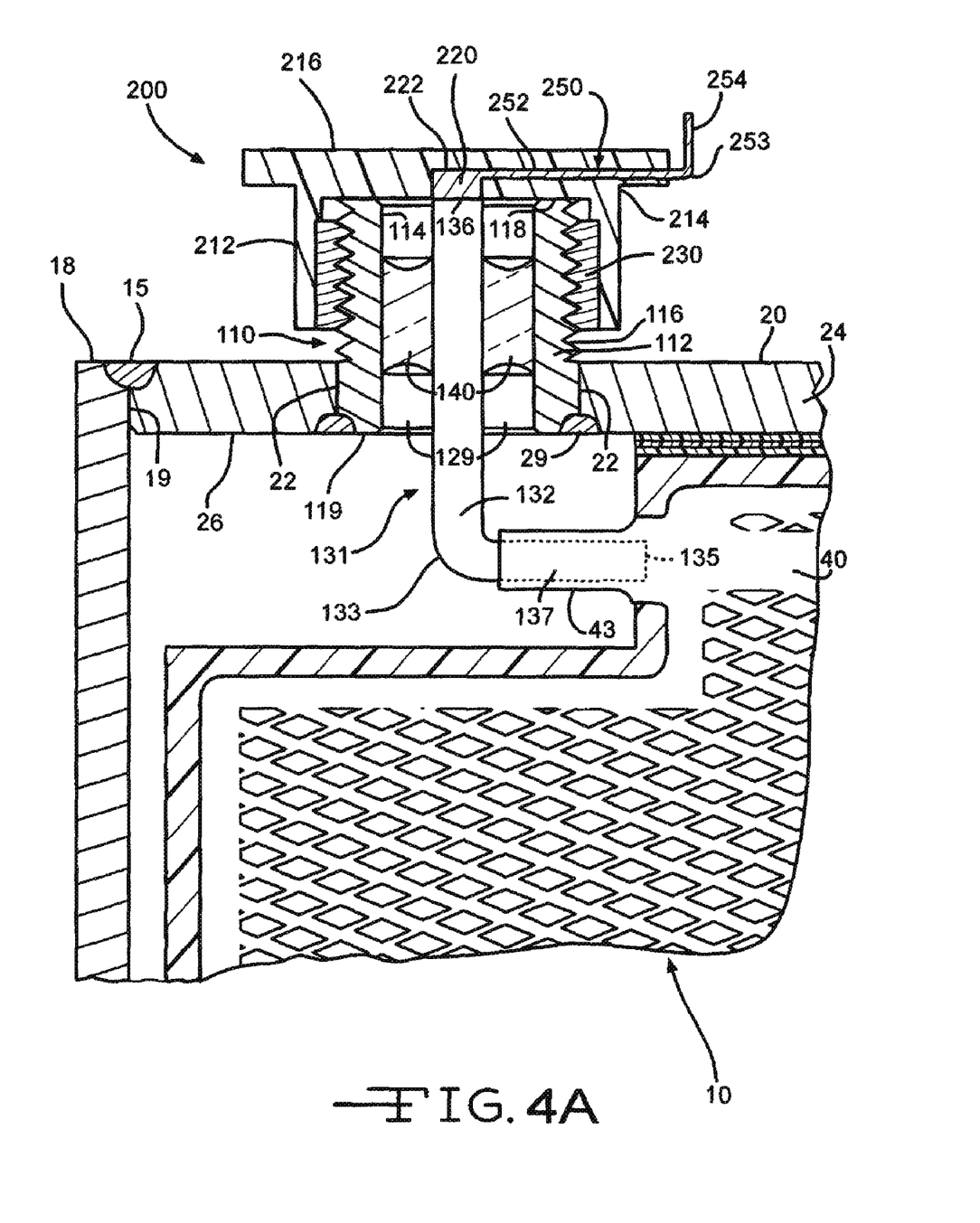
FIG. 4A is a side cross-sectional view of a cell that is an alternative to the cell of FIG. 4, the cell including a terminal assembly mated to the terminal connector depicted also in FIG. 4.

In one embodiment depicted in FIGS. 3, 4, and 4A, the exterior surface 116 of the ferrule 110 is provided with threads 122 and the inside of the hollow cylindrical body 212 of the mating terminal connector is correspondingly provided with matching threads 232 to enable a threaded connection between the terminal connector 200 and the ferrule 110.

In another embodiment, the ferrule is formed as the male fitting of a Bayonet Neill Concelman connector. Such a connector, also known as a BNC connector, is a standard industrial electrical connector often used in the transmission of high fidelity electrical signals, such as radio frequency signals. The BNC connector is a type of bayonet connector, named after the resemblance to the standard twist-on attachment for a bayonet.

Figure 9:
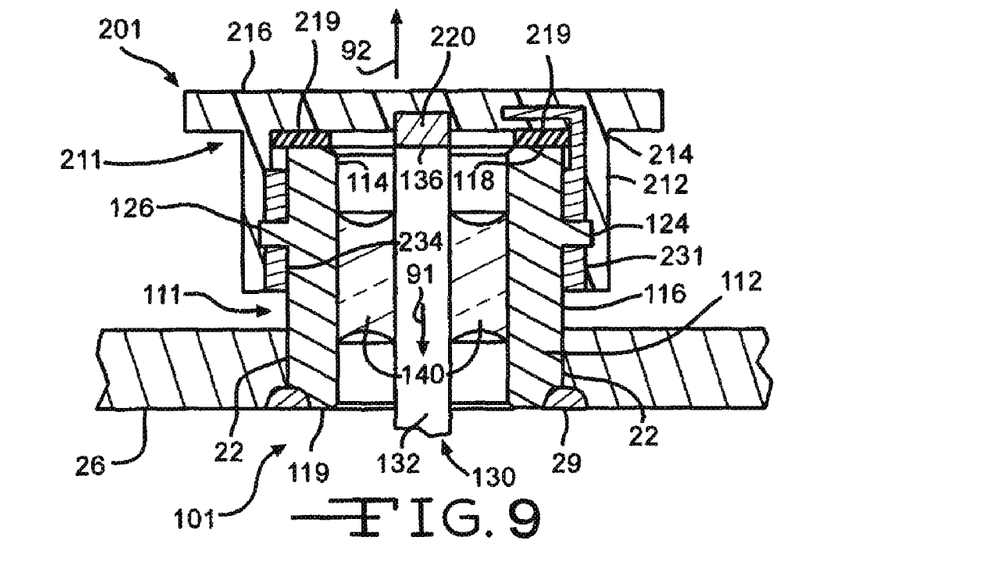
FIG. 9 is a side cross-sectional view of a third alternative embodiment of a terminal connector of the present invention using a BNC configuration connected to a cell's terminal assembly.
Figure 10A:
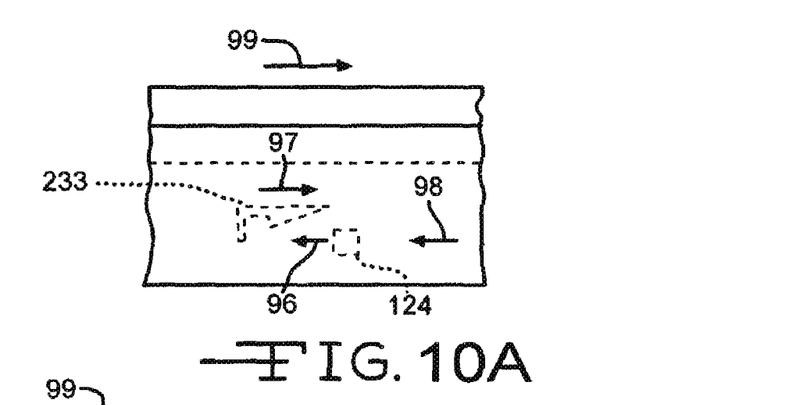
FIGS. 10A-10C are detailed side elevation views of the engagement means for securing the mating terminal connector of FIG. 9 to the cell's terminal assembly.
Figure 10B:
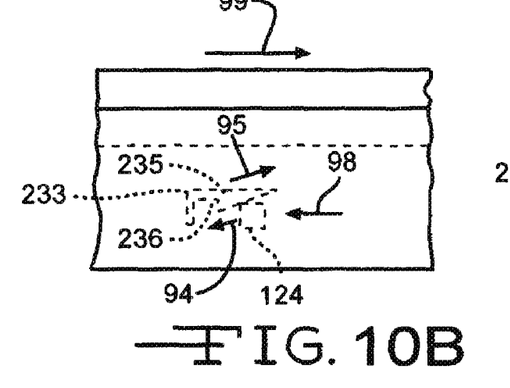
Figure 10C:
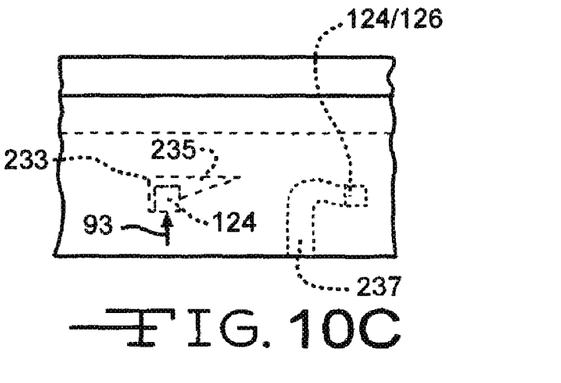

FIG. 9 is a side cross-sectional view of a BNC connector embodiment of the terminal connector of the present invention connected to a corresponding alternative BNC mating connector. FIGS. 10A-10C are detailed side elevation views of the engagement of means for securing the terminal connector 201 of FIG. 9 to the cell's terminal assembly 101. The terminal assembly 101 is similar to the terminal assembly 100 previously described herein and shown in FIGS. 3-4A, and is comprised of ferrule 111, terminal pin 130, and hermetic sealing material 140. Ferrule 111 includes an exterior surface 116, an interior surface 114, an outer end 118, and an inner end 119. Mating terminal connector 201 is similar to terminal connector 200 previously described herein and shown in FIG. 4, and is comprised of non-conductive cap 211 including a hollow cylindrical body 212 covered at an outer end 214 by a flange 216, a center terminal 220 embedded in the flange 216 and a perimeter terminal 231 disposed within the hollow cylindrical body 212 of the cap 211.

In lieu of threads 122 as shown on ferrule 110 of the terminal assembly 100 of FIG. 3, ferrule 111 is provided with a smooth exterior surface 116, from which protrudes a first pin 124 and a second pin 126, spaced at about 180 degrees opposite each other. When the terminal connector 201 is first brought into contact with the cell's terminal assembly 101, pin 124 is separated slightly from an engagement latch 233 formed on the inner surface 234 of perimeter terminal 231, as shown in FIG. 10A. A twisting motion of the terminal connector 201 relative to terminal connector 101 is performed, as indicated by arrows 99 and 98, causing pin 124 and engagement latch 233 to approach each other as indicated by arrows 97 and 96. When pin 124 makes contact with engagement latch 233 as indicated in FIG. 10B, the tang 235 is displaced diagonally upwardly relative to pin 124 as indicated by arrows 95 and 94. When pin 124 reaches slot 236, pin 124 pops into slot 236 as indicated by arrow 93 in FIG. 10C, and pin 124 is engaged with tang 235 of engagement latch 233. In a like manner, a similar engagement latch (not shown) is provided on the inner surface 234 of perimeter terminal 231 about 180 degrees opposite latch 233 for engagement with pin 126 of ferrule 111 of the terminal connector 101.

Referring again to FIG. 10C, in an alternative embodiment of the BNC connector configuration, perimeter terminal 231 is provided with a pair of slots such as slot 237 with which pins 124 and 126 are engaged. Such a slotted configuration is commonly used in the female BNC connectors such as mating terminal connector 201.

Referring again to FIG. 9, for either configuration of the BNC connector assembly, the mating terminal connector 201 is preferably provided with an elastomeric flat washer 219, which provides an axial force that helps to secure connector 201 to the terminal assembly 101. When mating terminal connector 201 is brought into contact with the cell's terminal assembly 101 and twisted in the previously described joining motion, elastomeric washer 219 is compressed. When the mating terminal connector 201 is fully engaged with the cell's terminal assembly 101 by the action of engagement latches or slots with pins 124 and 126, elastomeric washer 219 remains compressed, thereby providing axial biasing forces against both the mating terminal connector 201 and terminal assembly 101. The biasing force applied by the elastomeric washer 219 to the terminal connector 201 is indicated by arrow 92, while the force applied by the washer 219 against the cell's terminal assembly 101 is indicated by arrow 91. These forces serve to retain pins 124 and 126 securely in the engagement latches 235, or in the slots 237 provided in the perimeter terminal 231 of the mating connector. It will be apparent that the mating terminal connector 201 is separable from the terminal assembly 101 by the application of a compressive axial force upon washer 219, and a twisting motion applied to mating terminal connector 201 that is opposite to the twisting motion previously described.

Figure 7:
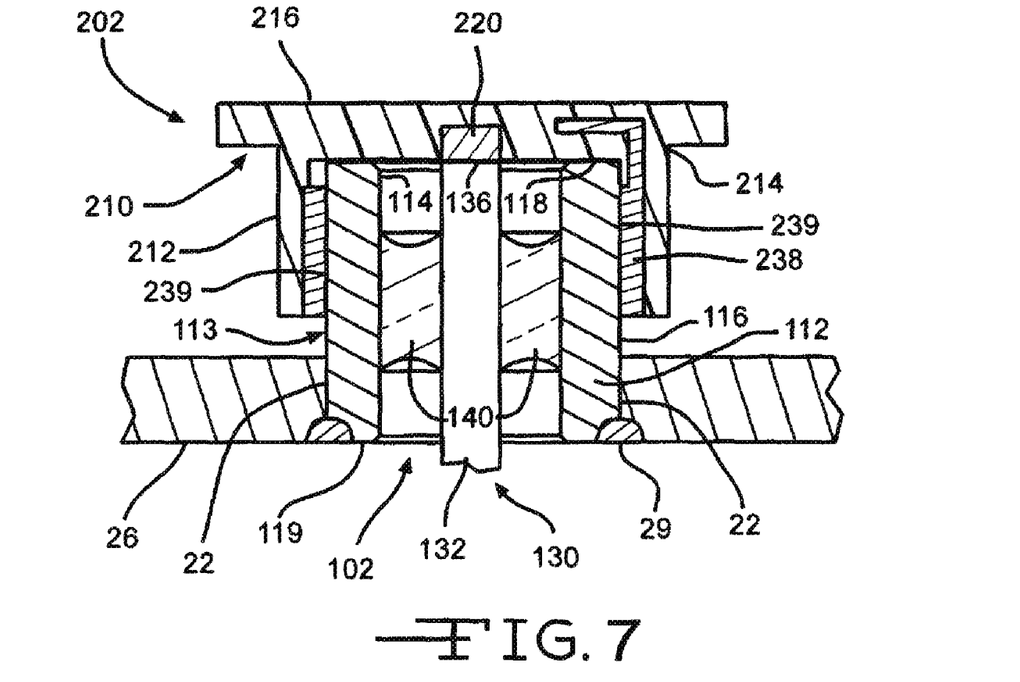
FIG. 7 is a side cross-sectional view of a first alternative embodiment of the terminal connector of the present invention connected by a press fit to a cell's terminal assembly.

In another embodiment of the present invention, the ferrule is provided with a smooth cylindrical surface, and the perimeter terminal of the terminal connector is provided with a smooth inner surface dimensioned such that the mating connector is press-fittingly engageable with the exterior surface of the ferrule. FIG. 7 is a side cross-sectional view of this alternative embodiment of the cell's terminal assembly connected by a press fit to a corresponding alternative mating terminal connector. The cell's terminal assembly 102 is similar to the terminal assembly 100 previously described herein and shown in FIGS. 3-4A, and is comprised of ferrule 113, terminal pin 130, and hermetic sealing material 140. Ferrule 113 includes an exterior surface 116, an interior surface 114, an outer end 118, and an inner end 119. The terminal connector 202 is similar to the terminal connector 200 previously described herein and shown in FIG. 4, and is comprised of non-conductive cap 210 including a hollow cylindrical body 212 covered at an outer end 214 by a flange 216, a center terminal 220 embedded in the flange 216 and a perimeter terminal 238 disposed within the hollow cylindrical body 212 of the cap 210.

In lieu of threads 122 as shown on ferrule 110 of the terminal connector 100 of FIG. 3, ferrule 113 of terminal assembly 102 of FIG. 7 is provided with a smooth exterior surface 116. Mating terminal connector 202 is provided with a corresponding smooth cylindrical interior surface 239 that is slightly smaller in diameter than the diameter of surface 116 of ferrule 113, such that the terminal connector 202 may be fitted to the cell's terminal assembly 102 by a mild press fit of ferrule 113 within perimeter terminal 238. As used herein, a mild press fit is a fit between two parts that is achievable by the application of forces easily delivered by a person's thumb and fingers. It will be apparent that the terminal connector 202 is separable from ferrule 113 by the application of similar forces applied in the opposite direction to those used in the connection with the cell's terminal assembly.

Figure 8:
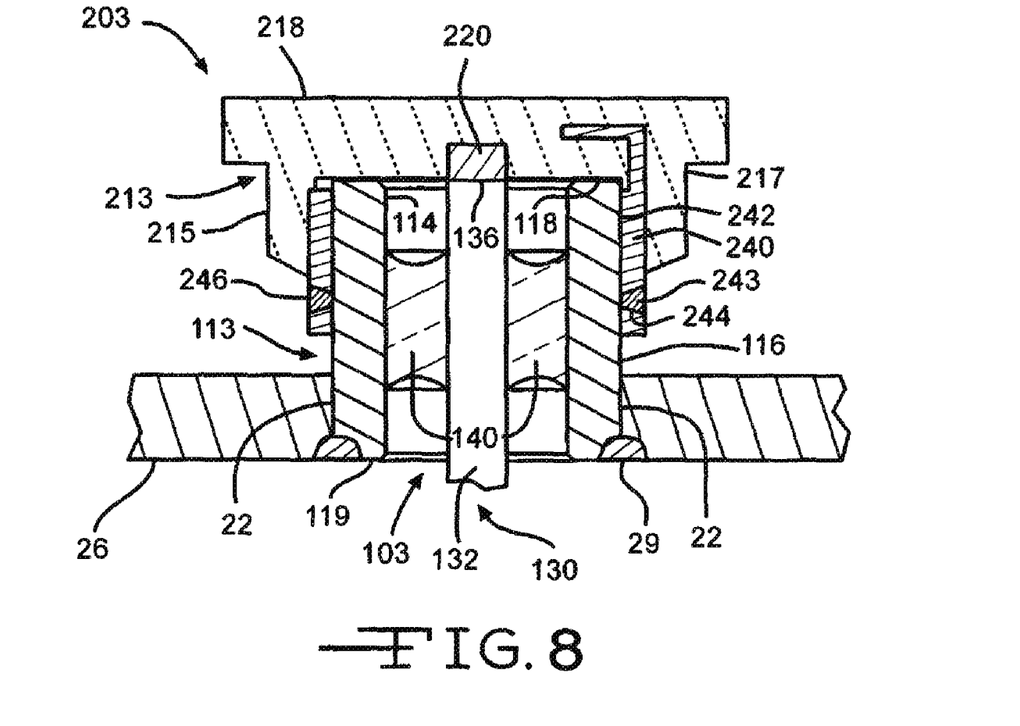
FIG. 8 is a side cross-sectional view of a second alternative embodiment of a terminal connector of the present invention connected by welding to a cell's terminal assembly.

If a permanent, rather than detachable electrical connection between the ferrule and the terminal connector is desired, the perimeter terminal of the mating terminal connector may be joined to the exterior surface of the ferrule by welding, soldering, or brazing. FIG. 8 is a side cross-sectional view of this alternative embodiment of the cell's terminal assembly 103 connected by welding to a corresponding alternative mating terminal connector. The cell's terminal assembly 103 is similar to the terminal assembly 102 previously described herein and shown in FIG. 7, and is comprised of ferrule 113, terminal pin 130, and hermetic sealing material 140. Ferrule 113 includes an exterior surface 116, an interior surface 114, an outer end 118, and an inner end 119. Mating terminal connector 203 is similar to the terminal connector 202 previously described herein and shown in FIG. 7, and is comprised of non-conductive cap 213 including a hollow cylindrical body 215 covered at an outer end 217 by a flange 218, a center terminal 220 embedded in the flange 218 and a perimeter terminal 240 disposed within the hollow cylindrical body 215 of the cap 213.

The mating terminal connector 203 is fitted to the cell's terminal assembly 103 by a mild press fit or a sliding fit between the interior surface 242 of perimeter terminal 240 and the exterior surface 116 of ferrule 113. To effect the permanent attachment of the terminal connector 203 to the cell's terminal assembly 103, a weld 243 is made which joins perimeter terminal 240 to ferrule 113. Weld 243 is preferably a plug weld made within a hole 244 that is provided in perimeter terminal 240 prior to the assembly operation. In the preferred embodiment, an additional plug weld 246 is made at a location 180 degrees around perimeter terminal 240; and additional plug welds (not shown) are made at equally spaced locations, such a e.g., four welds spaced at 90 degree intervals.

In the embodiment depicted in FIG. 8, the cap 213 of the terminal connector 203 is preferably made of a ceramic material rather than a plastic, in order to prevent melting, decomposition or other thermal damage to cap 213 during the welding process. Suitable ceramic materials include, but are not limited to alumina, titania, zirconia, silicon nitride, and silicon carbide.

Each of the terminal assemblies and mating terminal connectors depicted in FIGS. 4, 7, 8, and 9 are dimensioned to ensure that an effective electrical contact (i.e. one essentially of zero resistance) is made between the cell's terminal pin and the center terminal of the mating terminal connector, and between the cell's ferrule and the perimeter terminal of the terminal connector. For the contact between the cell ferrule and the perimeter terminal of the mating terminal connector, for each of the embodiments depicted in FIGS. 4, 7, 8, and 9, such effective electrical contact is easily ensured, by virtue of the extensive engagement of the respective surfaces with each other.

In the embodiment 150 of FIG. 4, threads 232 of the mating terminal connector 200 make firm and extensive contact with threads 122 of ferrule 110. In the embodiment of FIG. 7, interior surface 239 of perimeter terminal 238 of the mating terminal connector 202 makes firm and extensive contact with surface 116 of the cell's ferrule 113, particularly due to the press fit between ferrule 110 and perimeter terminal 238. In the embodiment of FIG. 8, interior surface 242 of perimeter terminal 240 of the terminal connector 203 makes firm and extensive contact with surface 116 of the cell's ferrule 113, particularly due to the welds 243 and 246 between ferrule 113 and perimeter terminal 240. In the embodiment of FIG. 9, interior surface 234 of perimeter terminal 231 of the mating terminal connector 201 makes firm and extensive contact with surface 116 of the cell's ferrule 111, particularly due to engagement of pins 124 and 126 of ferrule 113 and the engagement latches 235 or slots 237 of the perimeter terminal 231.

For the contact between the terminal pin 130 of the cell's terminal assembly and the center terminal 220 of the mating terminal connector, for each of the embodiments depicted in FIGS. 4, 7, 8, and 9, such effective electrical contact must be attained by proper dimensioning of the respective terminal assemblies and mating terminal connectors. This point will be illustrated with reference to the embodiment of FIG. 4, but is equally applicable to those of FIGS. 7, 8, and 9.

Referring to FIG. 4, when the mating terminal connector 200 is fitted to the cell's terminal assembly 100, center electrical contact 220 must be brought into forced contact with outer end 136 of terminal pin 130, in order to achieve effective electrical contact between these two conductors. This is most simply accomplished by having outer end 136 of terminal pin 130 function as a stop against center electrical contact 220 of the mating terminal connector 200. In other words, when the mating terminal connector 200 is fitted to the cell's terminal assembly 100, it is the outer end 136 of the terminal pin 130 coming into contact with center electrical contact 220 that stops the axial movement of the terminal connector 200 toward the cell's terminal assembly 100.

In one embodiment, center electrical contact 220 is made flush (i.e. coplanar) with inner surface 209 of flange 210 of the mating terminal connector 200. In order for the outer end 136 of the terminal pin 130 to act as a stop against center electrical contact 220 of the mating terminal connector 200, outer end 136 of terminal pin 130 protrudes slightly beyond the plane defined by the end 118 of ferrule 100. Accordingly, when the terminal connector 200 is threadedly engaged with ferrule 200, the rotation of mating connector 200 on ferrule 110 will be stopped because of contact between the outer end 136 of the terminal pin 130 and center electrical contact 220 of the mating terminal connector 200. A small additional tightening torque applied to the terminal connector 200 will firmly force center electrical contact 220 against the end 136 of the terminal pin 130, thereby ensuring effective electrical contact there between. In this embodiment, it is preferred that the outer end 136 of the terminal pin 130 protrudes at least about 0.020 inches beyond the plane defined by the end 118 of ferrule 100 in order to provide effective electrical contact.

In another embodiment (not shown), the outer end 136 of the terminal pin 130 may be recessed beneath the plane defined by the outer end 118 of ferrule 110. In this embodiment, center electrical contact 220 of the mating terminal connector 200 protrudes beyond inner surface 209 of flange 210 a corresponding distance such that when the terminal connector 200 is threadedly engaged with ferrule 200, the rotation of the connector 200 on ferrule 110 is stopped by contact between the outer end 136 of the terminal pin 130 and center electrical contact 220 of the terminal connector 200. The distance which center electrical contact 220 protrudes beyond inner surface 209 of flange 210 is preferably at least about 0.020 inches greater than the distance that outer end 136 is recessed beneath the plane defined by the outer end 118 of ferrule 110. In this manner, substantially the same effective electrical contact is provided between the end 136 of the terminal pin 130 and the center electrical contact 220 as is provided in the previously described embodiment.

It will be apparent that although the attainment of effective electrical contact between the terminal pin 130 of the cell's terminal assembly 100 and the center electrical contact 220 of the mating terminal connector 200 has been illustrated with reference to the embodiment of FIG. 4, these principles are equally applicable to the embodiments of FIGS. 7, 8, and 9.

Figure 5:
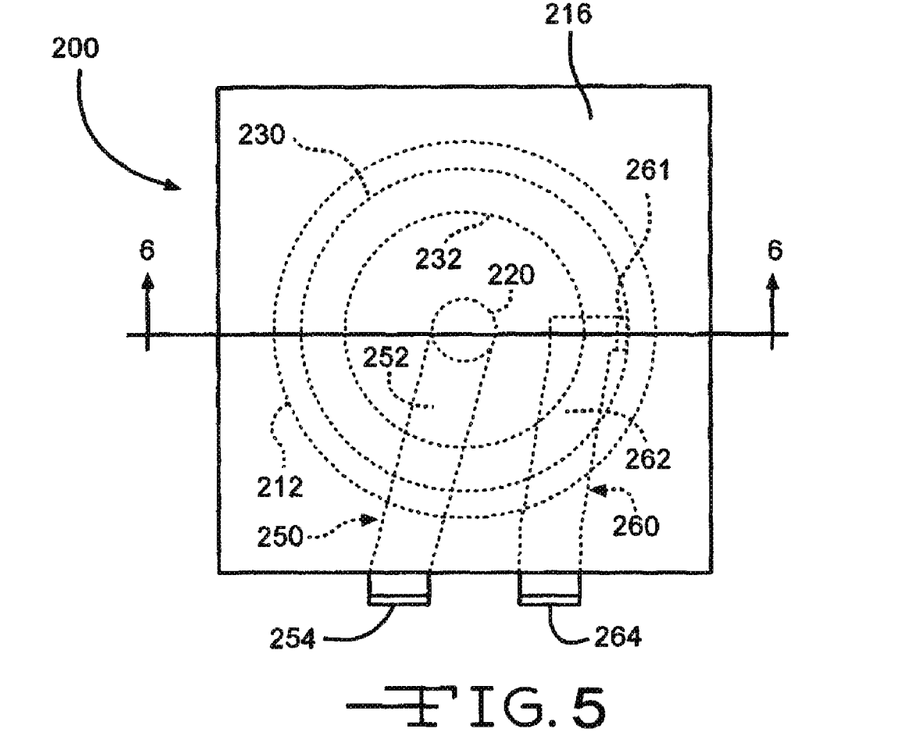
FIG. 5 is a top view of the terminal connector of FIGS. 1, 2, 4, and 4A, depicting conductors provided for connection to a device to be powered by an electrochemical cell.
Figure 6:
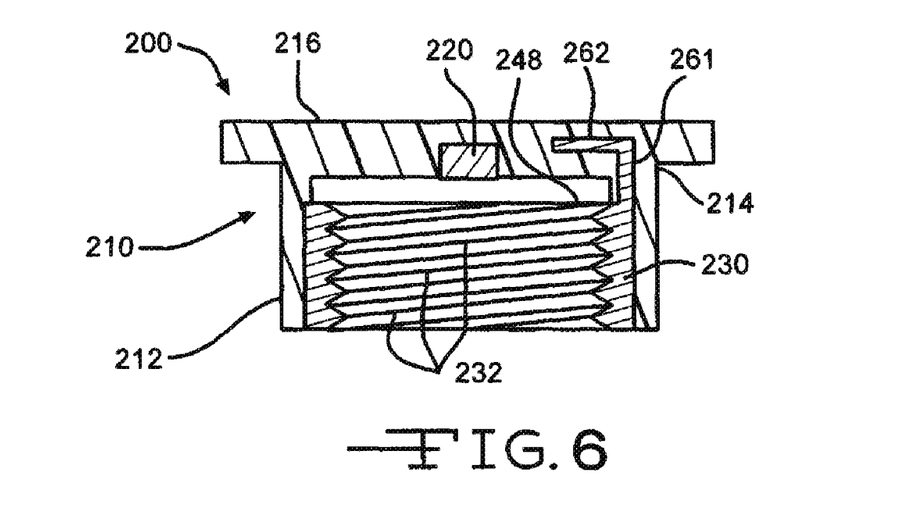
FIG. 6 is a side cross-sectional view of the terminal connector of FIG. 2 and FIG. 5, taken along line 6-6 of FIG. 5.

To facilitate connection of the cell's terminal assembly to an external device to be powered by the cell, the mating terminal connector preferably further comprises a first conductor extending from the center terminal through the flange of the cap, and a second conductor extending from the perimeter terminal through the flange of the cap. FIG. 5 is a top view of the mating terminal connector 200 of FIGS. 1, 2, 4, and 4A, depicting such conductors provided for connection to a device to be powered by a cell. FIG. 6 is a side cross-sectional view of the terminal connector 200 of FIG. 2 and FIG. 5, taken along line 6-6 of FIG. 5.

Referring in particular to FIGS. 4, 5, and 6, center contact 220 is joined to first conductor 250, which comprises an elongated horizontal bar 252 that extends from an upper edge 222 of center contact 220, an elbow 253, and an elongated vertical tab 254. The majority of elongated horizontal bar 252 is embedded within flange 216 of cap 210, with a short section protruding from flange 216 proximate to elbow 253. In the preferred embodiment, center contact 220 and first conductor 250 are integrally formed as a single piece, and insert molded into the desired position when cap 210 is formed. Cap 210 is preferably made of an injection moldable or curable polymer, such as polysulfone, polyetheretherketone, or polyurethane.

Perimeter contact 230 is joined to second conductor 260, which comprises a short vertical section 261 that extends from an upper edge 248 of perimeter contact 230, an elongated horizontal bar 262, an elbow 263 (see also FIG. 1), and an elongated vertical tab 264. The majority of elongated horizontal bar 262 is embedded within flange 216 of cap 210, with a short section protruding from flange 216 proximate to elbow 263. In the preferred embodiment, perimeter contact 230 and second conductor 260 are also integrally formed as a single piece, and insert molded into the desired position when cap 210 is formed.

The elongated tabs 254 and 264 of the first and second conductors 250 and 260 are adapted for connection into an electrical receptacle (not shown). The electrical receptacle typically is comprised of a pair of slots in a circuit board dimensioned so as to permit the elongated tabs of the conductors to be "plugged" into them. The center contact 220, the perimeter contact 230, and the electrical conductors 250 and 260 of the mating terminal connector may be made of stainless steel or titanium, or other suitable metals are described previously herein for the ferrule 110 and the terminal pin 130.

The embodiments described herein may be used with a variety of cells. In general, such a cell is comprised of a conductive casing closed at one end and having an opening at the opposite end thereof closed by a conductive lid. The conductive lid is comprised of a wall having an inside surface, an outside surface, and an opening therethrough from the inside surface to the outside surface to which the cell's terminal assembly is joined and sealed; an electrode assembly housed inside the casing and comprised of a first electrode of a first polarity including a currant collector and a second electrode of a second, opposite polarity. The current collector includes a coupling element for connection to the terminal pin. The open volume within the conductive casing is filled with an electrolyte to activate the electrode assembly.

The cell may be configured with a case-negative or case-positive ground configuration. The cell may be comprised of a simple sandwich-like rectilinear electrode structure, such as is disclosed in the aforementioned U.S. Pat. No. 5,250,373 to Muffoletto et al. Alternatively, the electrodes may be configured in a jellyroll arrangement, such as is disclosed in U.S. Pat. No. 6,951,576 to Takeuchi, which is assigned to the assignee of the present invention and incorporated herein by reference. In another embodiment, the electrodes may be configured in a serpentine arrangement such as is disclosed in the aforementioned U.S. Pat. No. 6,929,881 to Wutz et al. In a cell in which the electrodes are configured in a serpentine arrangement, the cell may further comprise a cathode bridge to facilitate connection of a current collector to the multiple cathode plates of the cell, as is disclosed in the aforementioned U.S. Pat. No. 6,004,692 to Muffoletto et al. It is to be understood that these suitable cell configurations are to be considered as exemplary and not limiting, and that the terminal connectors may be adapted to many other cell configurations.

FIG. 4A is a side cross-sectional view of a cell that is an alternative to the cell of FIG. 4. The cell 10 includes a terminal assembly connected to the mating terminal connector 200 also depicted in FIG. 4. Terminal pin 131 differs from terminal pin 130 of the cell of FIG. 4, in that it includes an elbow 133 proximate to the inner end 135 thereof. This feature aligns the inner section 137 of the terminal pin 131 with the coupling element 43 of current collector 40, thereby providing a greater length of contact between the terminal pin 131 and current collector 40 at which a bond may be formed. An example of such a terminal pin and current collector configuration and bond is provided in the aforementioned U.S. Pat. No. 5,250,373 to Muffoletto et al.

It is, therefore, apparent that there has been provided, in accordance with the present invention, a coaxial electrical connector fitting for connection to a cell used in implantable medical devices. While this invention has been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

What is claimed is:

1. A terminal connector that is matable to a ferrule and a conductive terminal pin of an electrochemical cell, the terminal connector comprising:
   a) a non-conductive body including a flange, the non-conductive body supporting a center conductive terminal embedded in the flange and a perimeter conductive terminal disposed within the body of the terminal connector;
   b) a first conductor extending from the center terminal through the flange of the non-conductive body;
   c) a second conductor extending from the perimeter terminal through the flange of the non-conductive body; and
   d) wherein the terminal connector is matable with a cell ferrule with the exterior surface of the ferrule being contactable to the perimeter terminal of the terminal connector and a terminal pin of the cell being contactable to the center terminal of the terminal connector.

2. The terminal connector of claim 1 wherein the perimeter terminal of the terminal connector is threaded to enable a threaded connection between the terminal connector and the ferrule of the cell.

3. The terminal connector of claim 1 wherein the terminal connector is formed as a BNC connector adapted to engage with protruding pins of the ferrule of the cell.

4. The terminal connector of claim 1 wherein the perimeter terminal is press-fittingly engageable with an exterior surface of the ferrule of the cell.

5. The terminal connector of claim 1 wherein the perimeter terminal is joinable to an exterior surface of the ferrule by a weld.

6. The terminal connector of claim 5 wherein the non-conductive body is made of ceramic.

7. The terminal connector of claim 1 wherein the first and second conductors are comprised of elongated tabs that are connectable to an electrical receptacle.

8. The terminal connector of claim 1 wherein the first and second conductors are of either titanium or stainless steel.

* * * * *